United States Patent [19]

Sass et al.

[11] 4,093,710

[45] June 6, 1978

[54] RAPID DISSOLVING EFFERVESCENT GRANULES

[75] Inventors: Robert N. Sass, Greenwood; Chwang Tek Wie, Lincoln, both of Nebr.

[73] Assignee: Sandoz, Inc., E. Hanover, N.J.

[21] Appl. No.: 703,255

[22] Filed: July 7, 1976

[51] Int. Cl.² .............................................. A61L 9/04
[52] U.S. Cl. .................................................... 424/44
[58] Field of Search ........................................ 424/44

[56] References Cited

U.S. PATENT DOCUMENTS

| 3,102,075 | 8/1963 | Millard | 424/44 |
|---|---|---|---|
| 3,401,216 | 1/1964 | Coletta | 424/44 |
| 3,708,574 | 1/1973 | Corker | 424/44 |
| 3,822,344 | 7/1974 | Corker | 424/44 |
| 3,903,255 | 9/1975 | Gusman | 424/44 |

*Primary Examiner*—Stanley J. Friedman
*Attorney, Agent, or Firm*—Gerald D. Sharkin; Robert S. Honor; Thomas O. McGovern

[57] ABSTRACT

Free flowing, rapid dissolving, effervescent granules in particular, potassium chloride granules, are prepared by granulating an alkali metal carbonate and/or bicarbonate and active ingredient with water containing a surfactant, such as polyethylene glycol 1540, and after drying mixing with a pharmaceutically acceptable organic acid plus additives.

16 Claims, No Drawings

RAPID DISSOLVING EFFERVESCENT GRANULES

This invention relates to free flowing granules which dissolve rapidly in water to yield a palatable effervescent solution.

This invention further relates to a method of preparing free flowing granules which dissolve rapidly in water to yield a palatable effervescent solution.

This invention relates, in particular, to free flowing, potassium chloride granules, which dissolve in cold water in about one minute without stirring to yield a palatable effervescent potassium chloride solution wherein the ratio of potassium ion to chloride ion is maintained in a ratio of 1 to 1.

This invention further relates to a method of preparing free flowing, rapid dissolving, palatable, potassium chloride effervescent granules, which dissolve in cold water in about one minute without stirring.

This invention also relates to free flowing potassium chloride granules in unit dose form which dissolve in water in about one minute to provide a palatable effervescent drink containing 11.7 to 40 milliequivalents of potassium chloride wherein the ratio of potassium ion to chloride ion is maintained at a rate of 1 to 1.

Effervescent powders or granules, such as potassium chloride powders or granules presently available for use in the treatment of potassium depletion or as a potassium supplement, require stirring to dissolve the granules within a reasonable time. Without stirring, the dissolution time for potassium chloride granules, for example, is in excess of 25 minutes. Granules, such as potassium chloride granules in unit dose form, which dissolve very rapidly without stirring in 3 to 4 ounces of water at drinking temperatures of about 35° to 75° F. would be very desirable, especially in hospitals where administration to large numbers of patients make stirring or long waiting time for dissolution unacceptable.

The present invention, accordingly, provides a method of preparing a free flowing, rapid dissolving, palatable effervescent granule having essentially the following composition per unit dose:

| Active Ingredient | Therapeutically effective amount |
|---|---|
| Alkali metal carbonate or bicarbonate | 0.200 Gm.–2.000 Gm. |
| Organic Acid, Anhydrous Granules | 0.200 Gm.–2.000 Gm. |
| Sweetener | 0.005 Gm.–0.100 Gm. |
| Surfactant | 0.002 Gm.–0.070 Gm. |
| Flavor | q.s. | which comprises:

(a) grinding the active ingredients, alkali metal carbonate, and sweetener to a mesh size of less than 80 (177 microns U.S. Std Sieve);

(b) mixing the active ingredient, alkali metal carbonate, and sweetener in a mixer to form a uniform mixture and granulating the mixture with a 1 percent to 25 percent by weight solution of the surfactant in water to form fine granules having a mesh size between 10 and 80;

(c) drying the fine granules at a temperature between 65° F. and 200° F. to a moisture level of less than 0.5 percent;

(d) sizing the granulation by grinding and screening the granules to obtain particles having a particle size of less than 20 mesh (U.S. Std Sieve) preferably a particle size distribution meeting the following specifications:

| PERCENT RANGE | MESH RANGE |
|---|---|
| 0 | Larger than 20 |
| 50–95 | 20–80 |
| 5–40 | 100–200 |
| Less than 10 percent | Smaller than 200 |

(e) sizing the anhydrous granular organic acid by grinding and screening to obtain particles having a particle size of less than 20 mesh, preferably a particle size distribution meeting the following specifications:

| PERCENT RANGE | MESH RANGE |
|---|---|
| 0 | Larger than 20 |
| 50–95 | 20–80 |
| 5–40 | 100–200 |
| Less than 20 | Smaller than 200 |

(f) milling the flavor to a particle size of less than 80 mesh; and (g) blending the granulation obtained in Step (d) with the acid and flavor of Steps (e) and (f) to obtain a uniform granule mixture.

The mesh sizes given above and below are all United States standard sieve mesh sizes.

In the above process, the active ingredients can be any pharmaceutical agent or nutrient which can or is normally administered in the form of an effervescent drink. The pharmaceutical agents would include, for example, aspirin, antacids, and antibiotics, such as penicillin, tetracycline, and the like. The granules of this invention are especially useful in the administration of potassium chloride in the treatment of potassium depletion as already indicated.

The alkali metal carbonate or bicarbonate in the above composition can be sodium or potassium carbonate or bicarbonate or mixtures thereof. In the potassium chloride granules, which are normally sodium free, potassium bicarbonate is the preferred alkali carbonate.

The preferred sweetener is saccharin, although other pharmaceutically acceptable sweeteners, such as dextrose, sucrose, and the like or mixtures of sweeteners can be used.

The surfactant used in the granulating solution of Step (b) can be any pharmaceutically acceptable surfactant which includes polyethylene glycols, such as polyethylene glycol 400, polyethylene glycol 1000, polyethylene glycol 1500, polyethylene glycol 1540, polyethylene glycol 4000, polyethylene glycol 6000, and polyethylene glycol 9000, myrj 52, myrj 52S, span 85, tween 20, tween 80, propylene glycol, dioctyl sodium sulfosuccinate, dioctyl calcium sulfosuccinate and sodium lauryl sulfate. The polyethylene glycols (PEG's) are the preferred surfactants in the present invention.

The organic acid used in the above process can be any pharmacologically acceptable acid which on contact with water will react to liberate carbon dioxide from the carbonate present causing effervesence and hence dissolution of the composition throughout the water and carbonation of the resultant solution. Suitable acids, which may be used singly or in combination, include citric acid, fumaric acid, adipic acid, malic acid, tartaric acid, and the like. The preferred acid for use in the instant invention is citric acid.

The flavor used in the granules of the instant invention can be amongst others, orange, lemon and lime, punch, pineapple, cherry, or mixtures of these. Artificial black cherry is the preferred flavor, especially Firmenich artificial black cherry 57.423/AP/05.51, which is commercially available.

The present invention, in particular, provides a method of preparing a free flowing, rapid dissolving, palatable effervescent potassium chloride supplement in granule form having the following composition per unit dose:

| | |
|---|---|
| Amino acid hydrochloride | 0.700 Gm.–3.000 Gm. |
| Potassium chloride, U.S.P. | 0.500 Gm.–2.500 Gm. |
| Potassium Bicarbonate, U.S.P. | 0.200 Gm.–2.000 Gm. |
| Citric Acid, U.S.P., Anhydrous | 0.200 Gm.–2.000 Gm. |
| Saccharin | 0.005 Gm.–0.100 Gm. |
| Polyethylene Glycol | 0.010 Gm.–0.070 Gm. |
| Flavor | q.s. | which comprises:

(a) grinding the amino acid hydrochloride, potassium chloride, potassium bicarbonate, and sweetener to a mesh size of less than 80;

(b) mixing the amino acid hydrochloride, potassium chloride, potassium bicarbonate, and sweetener in a mixer to form a uniform mixture and granulating the mixture with a 1 percent to 25 percent by weight solution of the polyethylene glycol in water to form fine granules having a mesh size between 10 and 60;

(c) drying the granules at a temperature between 65° F. and 200° F. to a moisture level of less than 0.5 percent;

(d) sizing the granulation by grinding and screening to obtain a particle size distribution meeting the following specifications:

| PERCENT RANGE | MESH RANGE |
|---|---|
| 0 | Larger than 20 |
| 50–95 | 20–80 |
| 5–40 | 100–200 |
| Less than 10 percent | Smaller than 200 |

(e) sizing the citric acid to obtain the following particle size distribution:

| PERCENT RANGE | MESH RANGE |
|---|---|
| 0 | Larger than 20 |
| 50–95 | 20–80 |
| 5–40 | 100–200 |
| Less than 20 | Smaller than 200 |

(f) milling the flavors to a particle size of less than 80 mesh; and (g) blending the granulation obtained in Step (d) with the acid and flavor of Steps (e) and (f) to obtain a uniform granule mixture.

In carrying out the above process, the amino acid hydrochloride, potassium chloride, potassium bicarbonate, and sweetener are ground to a mesh size of less than 80, preferably betwee 100 to 325 using standard comminuting equipment.

The amino acid hydrochloride used can be L-glycine hydrochloride, L-betaine, or other such amino acids as disclosed in U.S. Pat. No. 3,822,344; but because of superior flavor and stability properties, L-lysine hydrochloride is the preferred amino acid.

The above ingredients are then mixed in a suitable pharmaceutical mixer adapted for wet granulation to form a uniform mixture. This mixture is then wet granulated to a particle size of between 10 to 60 mesh, preferably between about 20 to 40 with a solution of polyethylene glycol in water. The polyethylene glycol used can be PEG 1000, PEG 1500, PEG 4000, PEG 6000, and the like, but PEG 1540 is especially preferred. The concentration of the solution used in the granulating process is about 1 to 25 percent, and the preferred solution contains approximately 10 percent to 15 percent by weight of PEG 1540 in water. In the granulating process, about 70 to 100 grams, preferably about 85 grams of the granulating solution are used per kilogram of combined weight of amino acid hydrochloride, potassium chloride, potassium bicarbonate, and saccharin. The final product of this invention contains from about 0.5 to 2.0 percent, preferably 0.75 to about 1.50 percent, in particular, from about 0.9 to 1.3 percent by weight of polyethylene glycol based on the final weight of the granules obtained by the instant invention.

Following the granulating step, the granules are dried preferably in a conventional hot air tray drier, using two drying cycles. The first cycle is carried out at about 70° F. and the second at about 150° F. to reach a moisture level of less than 0.5 percent by weight, preferably 0 to 0.2 percent. The drying step normally takes from about 16 to about 20 hours.

After the granules have been dried to the desired moisture level, the granules are then sized using standard pharmaceutical comminuting and screening equipment to obtain granules having the particle size indicated above.

The flavor and citric acid are sized using standard comminuting and screening equipment to obtain granules having the required particle size. The citric acid used is anhydrous and granular and the flavor is Firmenich artificial black cherry 57.423/AP/05.51, which is commercially available.

After the granules containing the amino acid hydrochloride, potassium chloride, potassium bicarbonate, and sweetener and the flavor and citric acid granules have been sized, they are blended to form a uniform granular mixture using conventional mixing apparatus. Following the final blending, the granules are packaged in suitable containers to protect the granules from moisture and stored in bulk in an area with a relative humidity of less than 15 percent at a temperature of about 60° to 75° F., preferably about 70° F.

The granules can thereafter be packaged in moisture resistant unit dose packages in a moisture controlled area having a relative humidity of less than 15 percent. The contents of each unit dose package provides a total of 11.7 to 40 milliequivalents of potassium chloride when dissolved in 3 to 4 ounces of drinking water. When packaged as indicated above, the granules remain free flowing and exhibit excellent stability over long periods of storage time; and when added to water, the granules dissolve rapidly to yield a palatable, pleasant tasting, effervescent drink useful in the treatment of potassium depletion. The preferred unit dose formulation has the following composition:

| | |
|---|---|
| L-lysine hydrochloride | 913 mg. |
| Potassium chloride | 1125 mg. |
| Potassium Bicarbonate | 500 mg. |
| Saccharin | 35 mg. |
| Polyethylene glycol-1540 (approximate) | 31 mg. |
| Black Cherry Flavor (Firmenich 57.423/AP/05.51) | 10 mg. |

| | |
|---|---|
| -continued | |
| Citric Acid | 550 mg. |

Each unit dose of the granules prepared from the above formulation provides 20 milliequivalents of potassium ion and 20 milliequivalents of chloride ions when dissolved in water.

EXAMPLE 1

Employing a Fitzpatrick Comminutor equipped with a #000 screen, 22 kilograms of L-lysine hydrochloride, 27 kilograms of potassium chloride, 12 kilograms of potassium bicarbonate and 0.84 kilograms of saccharin are ground to a fine powder having a particle size of less than 80 mesh.

The fine powders are transferred to a Lodige mixer and blended for 5 minutes. To this mixture are added approximately 5.5 kilograms of a 13.6 percent by weight solution of polyethylene glycol 1540 in water over a period of 5 to 10 minutes followed by a mixing cycle of about 20 minutes to form fine granules having a mesh size between about 16 to 40.

The wet granules are transferred to a Colton hot air tray drier, where they are dried at a temperature of approximately 70° F. for about 8 hours followed by a second drying cycle at about 150° F. for approximately 8 hours. The dried product has a moisture content of about 0.3 percent.

After drying, the granules are passed through a vibrating machine equipped with a 20 mesh screen and the particles larger than 20 mesh are ground with a Fitzpatrick Comminutor using a #0050 screen to obtain granules having the following particle size distribution:

| PERCENT RANGE | MESH RANGE |
|---|---|
| 0 | Larger than #20 |
| 50–95 | #20–#80 |
| 5–40 | #100–#200 |
| Less than 10 | Smaller than #200 |

Using a Fitzpatrick Comminutor equipped with a #0040 screen 13.2 kilograms of citric acid are sized and then screened to obtain the following particle size distribution:

| PERCENT RANGE | MESH RANGE |
|---|---|
| 0 | Larger than #20 |
| 50–95 | #20–#80 |
| 5–40 | #100–#200 |
| Less than 20 | Smaller than #200 |

About 500 grams of flavor is milled using a Fitzpatrick Comminutor with a #0040 screen to a particle size smaller than 80 mesh. Then 240 grams of the flavor; 13.2 kilograms of citric acid; and 62.59 kilograms of the dried granulation mixture are blended in a Hobart Mixer for 5 to 10 minutes, after which the granules are stored in moisture-proof containers at a temperature of approximately 70° F., and a relative humidity of less than 15 percent.

The granules are subsequently packaged under controlled relative humidity conditions of less than 15 percent in moisture proof aluminum strip packages using standard packaging equipment. Each package contains approximately 3.17 grams of stable free flowing granules, which when added to 3 to 4 ounces of cold drinking water dissolves in approximately one minute without stirring to form a pleasant tasting effervescent drink that provides 20 milliequivalents of potassium ion and 20 milliequivalents of chloride ion.

What is claimed is:

1. A method of preparing stable, free flowing, rapid dissolving, palatable effervescent granules having essentially the following composition per unit dose:

| | |
|---|---|
| Active ingredient suitable for administration orally in an effervescent drink | Therapeutically effective amount |
| Alkali metal carbonate or bicarbonate | 0.200 Gm. – 2.000 Gm. |
| Organic Acid, Anhydrous granule | 0.200 Gm. – 2.000 Gm. |
| Sweetener | 0.005 Gm. – 0.100 Gm. |
| Surfactant | 0.002 Gm. – 0.070 Gm. |
| Flavor | q.s. | which comprises:
(a) grinding the active ingredients, alkali metal carbonate, and sweetener to a mesh size of less than 80;
(b) mixing the active ingredient, alkali metal carbonate, and sweetener in a mixer to form a uniform mixture and granulating the mixture with a 1 percent to 25 percent by weight solution of the surfactant in water to form fine granules having a mesh size between #10 and #80;
(c) drying the granules at a temperature between 65° F. and 200° F. to a moisture level of less than 0.5 percent;
(d) sizing the granulation by grinding and screening to obtain particles having a particle size of less than 20 mesh;
(e) sizing the organic acid to obtain particles having a particle size of less than 20 mesh;
(f) milling the flavors to a particle size of less than 80 mesh; and
(g) blending the granulation of Step (d) with the acid and flavors of Steps (e) and (f) to obtain a uniform granule mixture.

2. The method according to claim 1 in which the alkali metal carbonate is a sodium or potassium carbonate or bicarbonate or mixtures thereof.

3. The method according to claim 1 in which the particles of Step (d) have the following particle size distribution:

| PERCENT RANGE | MESH RANGE |
|---|---|
| 0 | Larger than 20 |
| 50–95 | 20–80 |
| 5–40 | 100–200 |
| Less than 10 percent | Smaller than 200. |

4. The method according to claim 1 in which the particles of Step (e) have the following particle size distribution:

| PERCENT RANGE | MESH RANGE |
|---|---|
| 0 | Larger than 20 |
| 50–95 | 20–80 |
| 5–40 | 100–200 |
| Less than 20 | Smaller than 200. |

5. A method according to claim 1 of preparing a free flowing, rapid dissolving, palatable effervescent potassium chloride supplement in granule form having the following composition per unit dose:

| | |
|---|---|
| Lysine Hydrochloride | 0.700 Gm.–3.000 Gm. |
| Potassium chloride, U.S.P. | 0.500 Gm.–2.500 Gm. |
| Potassium Bicarbonate, U.S.P. | 0.200 Gm.–2.000 Gm. |
| Citric Acid, U.S.P., Anhydrous | 0.200 Gm.–2.000 Gm. |
| Sweetener | 0.005 Gm.–0.100 Gm. |
| Polyethylene Glycol | 0.010 Gm.–0.070 Gm. |
| Flavor | q.s. | which comprises:

(a) grinding the amino acid hydrochloride, potassium chloride, potassium bicarbonate, and sweetener to a mesh size of less than 80;

(b) mixing the amino acid hydrochloride, potassium chloride, potassium bicarbonate, and sweetener in a mixer to form a uniform mixture and granulating the mixture with a 1 percent to 25 percent by weight solution of the polyethylene glycol in water to form fine granules having a mesh size between 10 and 80;

(c) drying the granules at a temperature between 65° F. and 200° F. to a moisture level of less than 0.5 percent;

(d) sizing the granulation by grinding and screening to obtain particles having the following particle size distribution:

| PERCENT RANGE | MESH RANGE |
|---|---|
| 0 | Larger than 20 |
| 50–95 | 20–80 |
| 5–40 | 100–200 |
| Less than 10 percent | Smaller than 200 |

(e) sizing the citric acid to obtain particles having the following particle size distribution:

| PERCENT RANGE | MESH RANGE |
|---|---|
| 0 | Larger than 20 |
| 50–95 | 20–80 |
| 5–40 | 100–200 |
| Less than 20 | Smaller than 200 |

(f) milling the flavor to a particle size of less than 80 mesh; and (g) blending the granulation of Step d) with the acid and flavor of Steps e) and f) to obtain a uniform granule mixture.

6. The method according to claim 5 in which the sweetener is saccharin.

7. The method according to claim 5 in which the polyethylene glycol is polyethylene glycol 1540.

8. A stable free flowing, rapid dissolving, palatable effervescent composition having essentially the following components and quantities per unit dose:

| Active ingredient suitable for administration orally in an effervescent drink | Therapeutically effective amount |
|---|---|
| Alkali metal carbonate | 0.200 Gm.–2.000 Gm. |
| Organic Acid, Anhydrous granule | 0.200 Gm.–2.000 Gm. |
| Sweetener | 0.005 Gm.–0.100 Gm. |
| Surfactant | 0.002 Gm.–0.070 Gm. |
| Flavor | q.s. | in the form of granules having a particle size of less than 20 mesh which dissolve in water in approximately one minute prepared in accordance with the process of claim 1.

9. The composition of claim 8 in which the alkali metal carbonate is sodium or potassium carbonate or bicarbonate.

10. The composition of claim 9 having the following components and quantities per unit dose:

| | |
|---|---|
| Lysine Hydrochloride | 0.700 Gm.–3.000 Gm. |
| Potassium chloride, U.S.P. | 0.500 Gm.–2.500 Gm. |
| Potassium Bicarbonate, U.S.P. | 0.200 Gm.–2.000 Gm. |
| Citric Acid, U.S.P., Anhydrous | 0.200 Gm.–2.000 Gm. |
| Sweetener | 0.005 Gm.–0.100 Gm. |
| Polyethylene Glycol | 0.010 Gm.–0.070 Gm. |
| Flavor | q.s. | in the form of granules having a particle size of less than 20 mesh which dissolve in drinking water in approximately 1 minute.

11. The composition of claim 10 in which the polyethylene glycol is polyethylene glycol 1540.

12. The composition of claim 10 in which the sweetener is saccharin.

13. The composition of claim 10 in which the granules have essentially the following particle size distribution:

| PERCENT RANGE | MESH RANGE |
|---|---|
| 0 | Larger than 20 |
| 50–95 | 20–80 |
| 5–40 | 100–200 |
| Less than 10 percent | Smaller than 200. |

14. The composition of claim 10 in which the composition has essentially the following quantities of components per unit dose:

| | |
|---|---|
| L-lysine hydrochloride | 913 mg. |
| Potassium chloride | 1125 mg. |
| Potassium Bicarbonate | 500 mg. |
| Saccharin | 35 mg. |
| Polyethylene glycol-1540 | 31 mg. |
| Black Cherry Flavor (Firmenich 57.423/AP/05.51) | 10 mg. |
| Citric Acid | 550 mg. |

15. The composition of claim 8 in which the surfactant is polyethylene glycol having a molecular weight of from 400 to 9000.

16. The composition of claim 10 in which the polyethylene glycol has a molecular weight of from 1000 to 6000.

* * * * *